United States Patent [19]

Witt

[11] Patent Number: 4,462,661
[45] Date of Patent: Jul. 31, 1984

[54] LASER PROTECTION GOGGLES
[75] Inventor: Frank Witt, West Columbia, S.C.
[73] Assignee: Instrument Flight Research, West Columbia, S.C.
[21] Appl. No.: 351,504
[22] Filed: Feb. 23, 1982
[51] Int. Cl.³ .............................................. G02F 1/13
[52] U.S. Cl. ............................. 350/331 R; 350/356; 350/332; 351/158; 2/432
[58] Field of Search .............. 350/330, 331 R, 332, 350/267, 353, 356; 351/44, 158; 2/432

[56] References Cited

U.S. PATENT DOCUMENTS

| | | | |
|---|---|---|---|
| 3,245,315 | 4/1966 | Marks et al. | 351/44 X |
| 4,071,912 | 2/1978 | Budmiger | 350/331 R X |
| 4,155,122 | 5/1979 | Budmiger | 350/331 R X |
| 4,237,557 | 12/1980 | Gordon | 350/332 X |
| 4,279,474 | 7/1981 | Belgorod | 351/44 X |

FOREIGN PATENT DOCUMENTS 2735985  3/1979  Fed. Rep. of Germany ... 350/331 R

*Primary Examiner*—John K. Corbin
*Assistant Examiner*—Richard F. Gallivan
*Attorney, Agent, or Firm*—Allegretti, Newitt, Witcoff & McAndrews, Ltd.

[57] ABSTRACT

The invention is a laser ray eye protection device comprised of a laser detector, voltage controlled lens or lenses, and related interconnecting circuitry. The lenses remain in the normally transparent state until a laser ray is sensed by the detector which energizes the lenses into a state of opacity by the interconnecting circuitry. The invention may take on numerous specific embodiments. Various partial modifications and combinations thereof are described.

7 Claims, 16 Drawing Figures

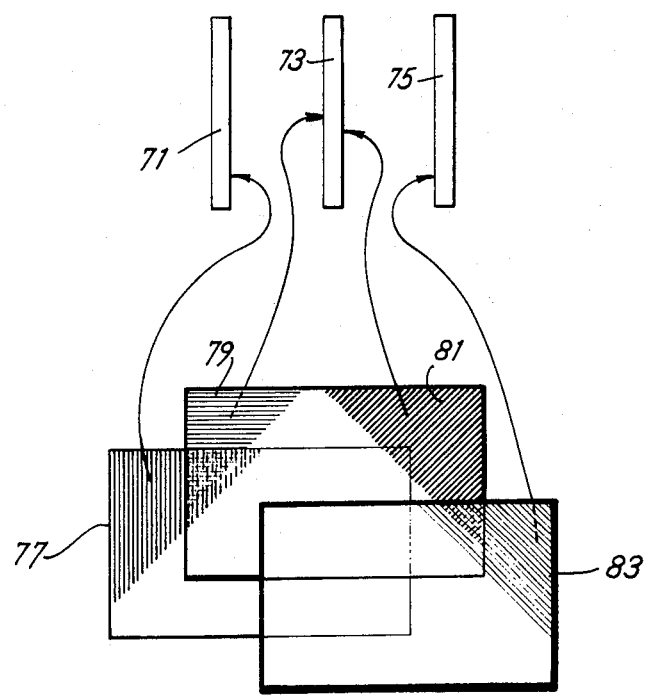
Fig. 14
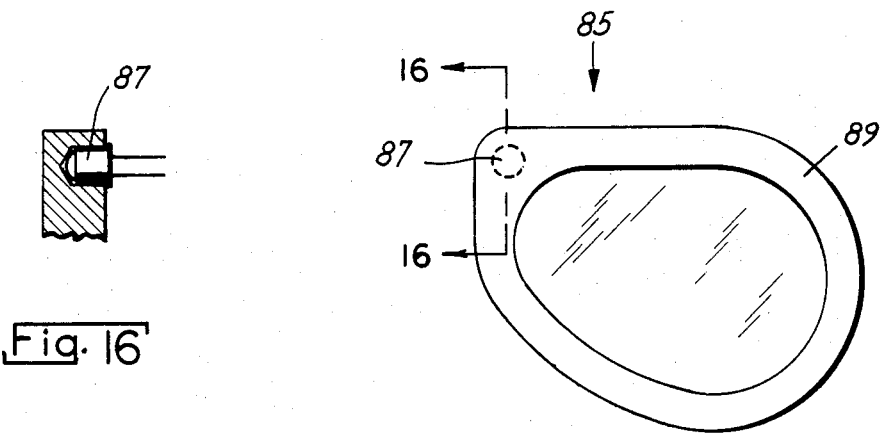
Fig. 16
Fig. 15

LASER PROTECTION GOGGLES

CROSS REFERENCE TO RELATED PATENTS AND PATENT APPLICATIONS

The following U.S. patents and pending patent application having same named inventor as the present application, are related to the present application in that a voltage controlled lens is utilized to provide dynamic scattering of light:
U.S. Pat. No. 4,021,935,
U.S. Pat. No. 4,106,217,
U.S. Pat. No. 4,152,846, and
U.S. patent application, Ser. No. 343,017, filed Jan. 26, 1982.

BACKGROUND OF THE INVENTION

The present invention relates to a pair of glasses worn by a person for eye protection against damage by laser rays, and more particularly relates to a liquid crystal lens configuration in combination with a laser radiation detector for blocking radiation from passing through the lens preventing eye injury.

The term, laser, refers to a process whereby a collimated beam of electromagnetic rays is amplified into a very narrow wavelength spectrum, having a high intensity. The intensities emitted pose a tremendous eye hazard. Despite purposeful avoidance of the laser rays, the rays may be received inadvertently by the eye either directly or from reflection.

Theoretically, laser rays can be made from any part of the electromagnetic spectrum—from the lowest frequency (radio waves) to the highest frequency (gamma waves). Currently, laser rays are made from the non-visible infrared and visible portions of the electromagnetic spectrum. It is expected that laser rays will be made from the ultraviolet portion of the spectrum in the near future.

Heretofore, eye protection from laser rays has been provided by a pair of goggles having a permanently darkened lens providing constant visual restriction. Such prior art goggles are sensitive to a single frequency of laser radiation. Different goggles must be used for each frequency encountered. Further, night time protection is unafforded by such prior art goggles due to the inherent visual restrictions accompanying the goggles.

It would be highly desirable to provide a device suitable for eye protection from laser rays without the accompanying visual restriction when laser rays are not present. Such protection from laser rays should be provided in general whether used for commercial, industrial, medical, military, or other purposes, and from laser rays of a broad electromagnetic spectrum. Particularly, it is desirable to provide such a device which not only would be effective in protecting the eyes from laser rays which presently exist, but also to provide the same adequate protection from laser rays of other wavelengths which presently are not used.

It is therefore an object of the present invention to provide an improved laser eye protection device.

It is yet another object of the present invention to provide a laser eye protection device which is responsive to a broad spectrum of laser frequencies.

It is yet another object of the present invention to provide a pair of laser protection goggles which may be used for night time protection.

It is a further object of the present invention to provide a laser protection device that is sensible and convenient to wear and which will not interfere with ordinary activity.

These and other objects of the present invention will become apparent from the following detailed description of the preferred embodiment.

SUMMARY OF THE INVENTION

The invention is a device for protecting the eyes from laser radiation. Protection is provided by means of a normally transparent voltage controlled lens which is switchable to an opaque state. A detector senses laser radiation and switches the lens to its opaque state.

BRIEF DESCRIPTION OF THE DRAWINGS

FIG. 14 depicts one example of the relative arrangement of alignment coatings in a two celled voltage controlled lens.

FIG. 15 is a diagram of a modified detector for use withe lens of FIG. 1.

FIG. 16 is a cross-sectional view along lines 16—16 of FIG. 15.

DETAILED DESCRIPTION OF THE PREFERRED EMBODIMENT

Figure 1:
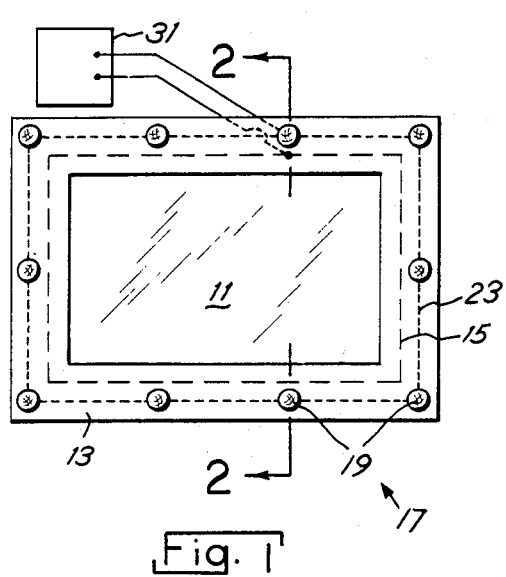
FIG. 1 is a front view of the basic form of the voltage controlled lens and detector of the preferred embodiment of the present invention.
Figure 2:
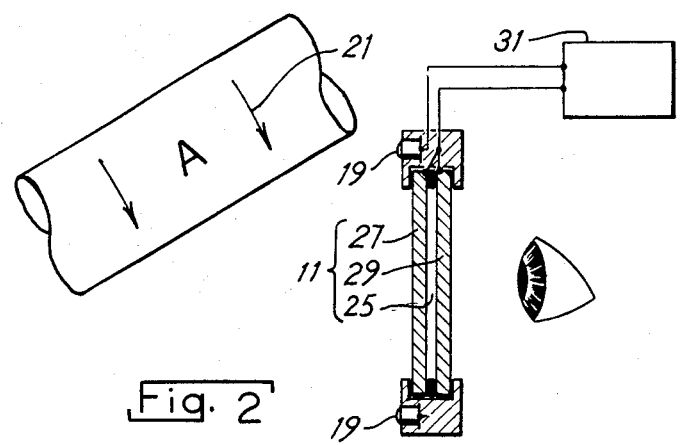
FIG. 2 is a cross sectional view of the lens of FIG. 1.

Referring to FIGS. 1 and 2, a voltage controlled lens 11 is set in a frame 13. The lens has a normally transparent state of light transmissiveness and is switchable to an opaque state for scattering light. The outer perimeter 15 of lens 11 extends within frame 13 as shown. The frame may be adapted to be held in front of the viewer's eyes by suitable means.

A primary detector 17 is constructed from an array of ambient omnidirectional photocells 19 and is positioned relative to frame 13 for sensing a laser beam moving onto lens 11. The photocells are arranged along a path 23 encompassing perimeter 15 of the lens, being equally spaced from one another. The distance between each photocell 19 is dependent on the minimum diameter of a laser ray bundle expected to be encountered by the wearer of the lens.

As shown in FIG. 2, photocells 19 are embedded within frame 13 such that their operational axes are substantially perpendicular to the plane of lens 11 which they are guarding. The photocells are conventional and are sensitive to any wavelength of laser intensity. When laser ray bundle "A" sweeps across the lens (as indicated by direction arrows 24), the ray bundle first crosses the guarded path 23 of the photocells prior to impinging lens 11. One or more of photocells 19 is actuated thereby causing the normally transparent lens to switch to its opaque state. The opaque state of the lens blocks the laser from passing through the lens to the wearer's eye.

Lens 11 is a conventional liquid crystal lens being formed of a transparent liquid crystal layer 25 which is sandwiched between a pair of flat panes 27, 29 of transparent solid material. The inner surfaces of the flat panes are each coated with a very thin layer of a transparent electrically conductive electrode. An alignment coating of transparent material is laminated over each electrode coating aligning the liquid, as described with reference to FIG. 14. An applied voltage to the electrode coatings will cause an electric current to flow through the liquid crystal layer causing a turbulence within the crystal making the lens structure opaque to light. This is referred to as a dynamic scattering of light.

The lens is switched to its opaque state by means of switching circuitry 31. Circuitry 31 includes a conventional voltage waveform generator for applying a waveform of a particular oscillating frequency across lens 11. In its opaque state, lens 11 scatters and breaks up laser ray bundle "A" so that it does not pose an eye hazard. When laser ray bundle "A" moves outside of the perimeter of primary detector 17, either by continued sweeping motion of bundle "A" or by the wearer of the device 10 turning his head so as to cause bundle "A" to move outside of the perimeter of primary detector 17, circuitry 31 disconnects the voltage waveform from lens 11 returning the lens to its normally transparent state.

Figure 7:
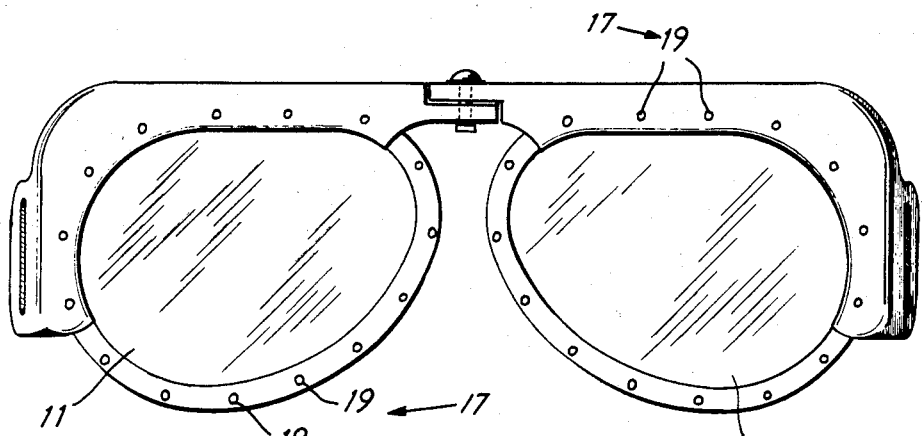
FIG. 7 is a front elevational view of the lens of FIG. 1 embodied in a pair of flight or laboratory glasses.

Circuitry 31 monitors actuation of photocells 19, such that the actuation of a single photocell prompts circuitry 31 to apply the voltage waveform to lens 11. Where a pair of lenses are used as shown in FIG. 7, circuitry 31 may control the lenses independent of one another.

Figure 13:
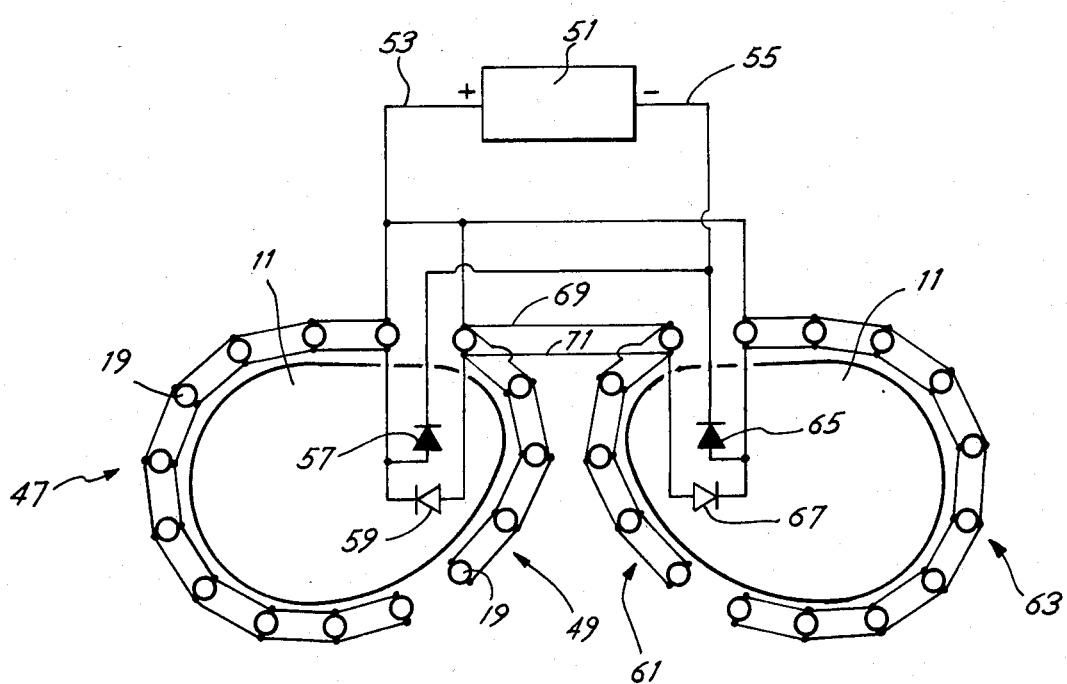
FIG. 13 is a partial schematic and block diagram of circuitry for a mask having two of the lenses of FIG. 1.

Referring to FIG. 13, photocells 19 are connected in two groups 47, 49 around each lens 11 of a dual lens system. A voltage source 51 places an output voltage across leads 53, 55 for attempting to actuate a light emitting diode 57. Each of photocells 19 of group 47 are electrically connected in parallel and connected between lead 53 and the anode of diode 57. The actuation of any one of photocells 19 by the laser beam closes the circuit path between lead 53 and diode 57 causing the diode to light.

Diode 57 serves as the switching portion of an optocoupler (not shown) which cause the liquid crystal lens to be energized to its opaque state whenever diode 57 is lit. As understood, the opto-isolator merely serves to connect the voltage generator across the electrode coatings of lens 11.

Group 49 of photocells 19 are similarly connected in parallel between lead 53 and diode 57 but via a blocking diode 59. Group 49 serves to actuate the lens 11 whenever one of its photocells is actuated by the laser beam. However, unlike group 47, group 49 also actuates the right lens 11. As the laser sweeps from left to right, group 47 is actuated first causing only the left lens to actuate to its opaque state. As the laser moves into group 49, the left lens remains opaque and the right lens is actuated to its opaque state. As the laser moves farther right on the right lens, the left lens clears.

A similar pair of groups 61, 63 of photocells 19 operate in a manner similar to groups 47, 49. Light emitting diode 65 and blocking diode 67 operate similar to diodes 57, 59. The two groups 49, 61 are connected together by leads 69, 71 such that each group 49, 61 serves to actuate both right and left lenses. The blocking diodes 59, 67 serve to prevent groups 47, 63 from actuating their non-associated right and left lens, respectively.

Figure 3:
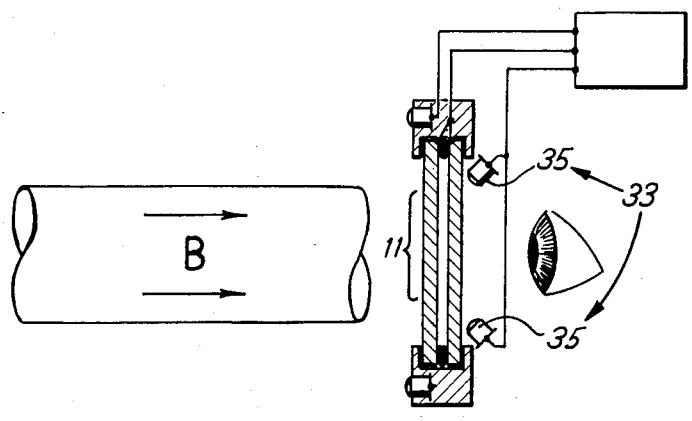
FIG. 3 is an enlarged partial cross sectional view of the lens of FIG. 2, which depicts a partial modification wherein multiple photocells are positioned behind the voltage controlled lens.

Referring to FIG. 3, in the unlikely event that the laser ray bundle does not move laterally across primary detector 17, as in the preceding discussion, but rather is so aimed as to constitute a direct hit (bundle "B") upon the voltage controlled lens, there is provided a secondary detector 33 constructed of a second array of like photocells 35 mounted by suitable means behind lens 11. Upon sensing the splash of bundle "B" upon the lens, secondary detector 33 in like manner as detector 17 causes lens 11 to transition to its opaque state. The electrical switching of circuitry 31 is responsive to an electrical signal from either of detectors 17 or 33.

As understood, the time of switching of the lens is a factor in the prevention of eye injury. The sweeping of bundle A as shown in FIG. 2 is very much slower than the direct hit of bundle B in FIG. 3. The detector 33 serves to opaque the lens after the front end of bundle B has passed through the lens. The size, intensity and angle of lens impingement of bundle B determines the effect, if any, of the front end of a direct hit by bundle B.

Figure 4:
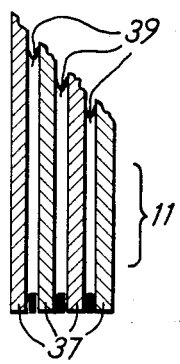
FIG. 4 is a cross sectional view, similar to FIG. 2, depicting a partial modification of the lens.

Referring to FIG. 4, voltage controlled lens 11 may be comprised of more than one cell. Whereas FIGS. 2 and 3 depict a single cell comprised of one liquid crystal layer 25, FIG. 4 depicts multiple cells comprised of alternate laminations of transparent solid material 37 and normally transparent liquid crystal material 39. As previously indicated, when a voltage is applied to the liquid crystal material, the lens changes from a normally transparent state to an opaque state. The degree of opacity is dependent on the thickness of the liquid crystal material. However, the response time required to transition from one state to another increases with the thickness of the liquid crystal material. For this reason cells are stacked as in FIG. 4, in order to provide a decrease in response time for the overall thickness of the lens system.

Figure 5:
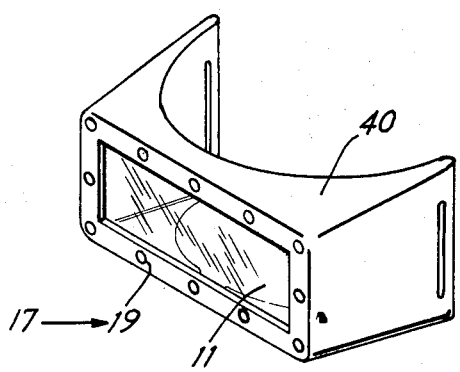
FIG. 5 is a pictorial view wherein the lens of FIG. 1 is embodied in a mask.

FIG. 5 depicts one of many possible specific embodiments of the invention in which a single lens 11 is mounted in a mask 40. Photocells 19 are positioned around the perimeter of the lens as shown.

Figure 6:
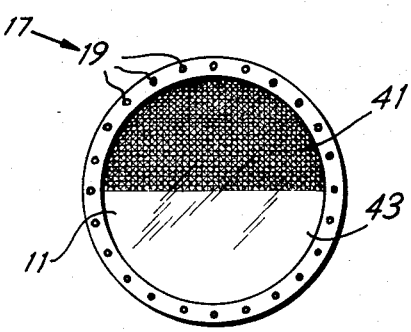
FIG. 6 is a front elevational view of a lens embodied in an observation window having segmented areas.

Having reference to FIG. 6 there is depicted another partial modification wherein voltage controlled lens 11 has upper and lower segmented areas 41, 43. Upper segment area 41 has been shaded to show that it is in the opaque state while lower segment area 43 remains clear. The lens can be segmented by using separate electrode coatings on respective segments 41, 43.

Detector 17 is wired so that when a laser ray bundle crosses the perimeter of the lens only the segment area 41 or 43 receiving the laser ray bundle is energized to the opaque state thereby providing uninterrupted visibility through the unaffected segment area. Many other shapes and numbers of segment areas are possible, as will suggest itself.

The wiring of the two segments 41, 43 for separate actuation may be similar to that of FIG. 13. Two groups similar to groups 47, 49 of photocells may control separate lens segments. Two light emitting diodes 57 may be used, one for each lens segment. One group of photocells actuates one diode 57 of an opto-coupler which switches the voltage waveform onto one of the lens segments; the other group of photocells actuates the other diode 57 of another opto-isolator which switches the voltage waveforms to the other lens segment.

Figure 8:
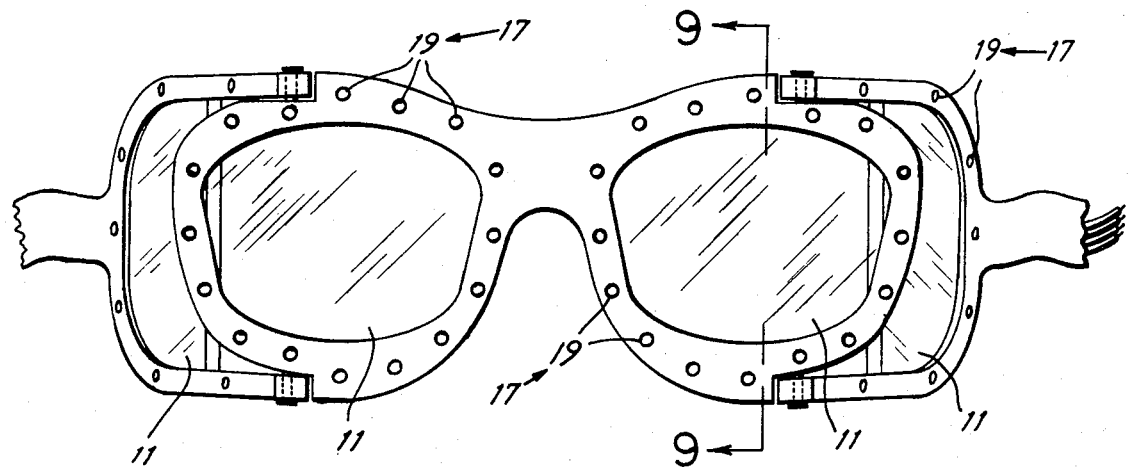
FIG. 8 is a front elevational view of the lens of FIG. 1 embodied in a pair of combat glasses.

Having reference to FIGS. 7 and 8, another partial modification is depicted wherein more than one voltage controlled lens 11 is incorporated into each laser ray eye protection device. Many other designs having multiple voltage controlled lenses 11 are possible.

As shown in FIGS. 7 and 8, each voltage controlled lens 11 has around its perimeter its own respective detector 17 to thereby provide for energization to the opaque state only that lens 11 or those lenses 11 which encounter a laser ray bundle, and therefore results in uninterrupted visibility through any unaffected lens 11.

Figure 9:
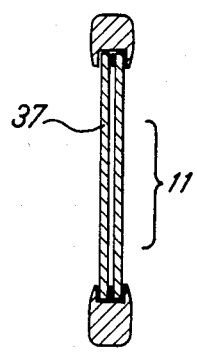
FIG. 9 is a cross sectional view of the lens of FIG. 8.
Figure 10:
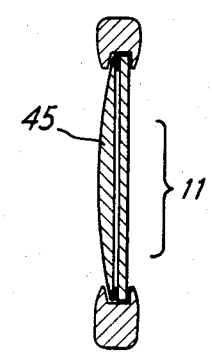
FIG. 10 is a cross sectional view, similar to FIG. 9, having a visual corrective lens.

Having reference to FIGS. 9 and 10, another partial modification is depicted wherein a standard transparent solid material 37 of FIG. 9 is replaced by a non-standard transparent solid material 45 in FIG. 10, so that visual correction, when needed, may be incorporated into the invention thus making the overall eye protection package more lightweight and compact for those who wear glasses. Many other designs and arrangements having corrective lenses 45 incorporated into the invention are possible.

Having reference to FIG. 14, alignment coatings, as discussed above, are indicated by close parallel lines on front views of superimposed glass panes 71, 73, 75. Alignment coating 77 is formed on pane 71 and is perpendicular to alignment coating 79 formed on the left face of pane 73. Liquid crystal (not shown) is positioned between panes 71 and 73 and between panes 73 and 75. Alignment coating 81 is positioned on the right face of pane 73 (the figure illustrates the two coatings 79, 81 on the same pane) and is perpendicular to alignment coating 83 formed on pane 75.

The three panes 71, 73, 75 may be said to form two cells which are bounded by alignment coatings 79, 81. As shown, the two alignment coatings 79, 81 are at approximately 45° to each other. As more cells are added, the alignment coatings bounding the cells may be set at various progressive angles. For example, the first two cells at 0° and 30°, the next cell set at 60°, the next cell set at 90° and so on to 330°. This arrangement of various angles of the alignment coatings aids in blocking laser bundles which strike the lens at an angle. Thus for maximum opacity, alignment coatings for each cell are placed at 90° to each other. When cells are stacked, bounding alignment coatings are placed at various angles to increase scattering of light.

The alignment coating is a transparent coating which is put over the underlying transparent electrode coating. When sufficient voltage is applied to the liquid crystal lens, the alignment coatings serve to align the molecules of the liquid material so that on opaque effect (dynamic scattering) is apparent.

Having reference to FIGS. 15 and 16, there is depicted another partial modification wherein the entire perimeter of the lens is guarded by an alternate dectector 85 comprised of a single photocell 87 imbedded in a transparent or translucent frame 89. Depending upon the length of the perimeter perhaps in some cases more than one photocell may be needed. When the frame is transparent, it is necessary to roughen the finish in order to provide a light scattering means. If the frame is translucent, a roughened finish is sometimes helpful but not as necessary since translucent material has an inherent light scattering property. Preferably, the light carrier is injection molded from acrylic.

In FIGS. 15 and 16, whenever a light bundle of laser intensity strikes any part of frame 89, some of the bundle is transmitted and scattered throughout the frame, thereby actuating detector photocell 87 which, in turn, signals the lens to change to its opaque state.

Figure 11:
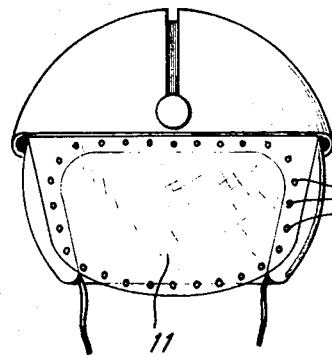
FIG. 11 is a front elevational view of the lens of FIG. 1 embodied in a helmet/visor combination.
Figure 12:
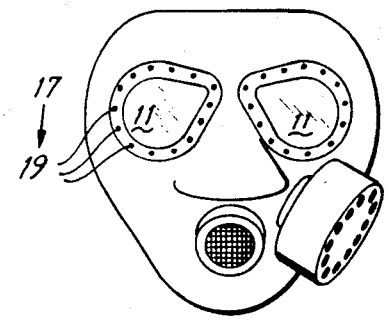
FIG. 12 is a front elevational view of the lens of FIG. 1 embodied in a gas mask.

FIGS. 11 and 12 are yet further possible specific embodiments of the invention which merely serve to illustrate the fact that the invention, per se, is not limited to any one or even a few embodiments, but the invention which is comprised of detector means, voltage controlled lens or lenses, and associated conventional electrical components, has in fact numerous designs, structures and arrangements which directly fall within the spirit and scope of the invention and appended claims.

Having thus described, the invention, what is claimed as new and desired by Letters Patent of the United States is set forth in the following claims.

What is claimed is:

1. A laser ray eye protection device comprising:
   voltage controlled lens means having a first state of transparency and a second state of opacity, said voltage controlled lens means being responsive to a switching signal for switching lens means from a normal state of transparency to a state of opacity;
   detector means including a plurality of photocells mounted by suitable means along a path encompassing the perimeter of said lens, said detector means being responsive to detected radiation for generating an energizing signal whenever a laser ray crosses said path; and
   switching means responsive to said energizing signal of said detector means for generating said switching signal.

2. An eye protection device as defined in claim 1, wherein said voltage controlled lens is comprised of multiple cells laminated together to provide decreased response time and increased opacity.

3. An eye protection device as defined in claim 1, and further including secondary detector means comprising a plurality of photocells mounted by suitable means behind said voltage controlled lens for monitoring laser radiation passing through said lens means to provide a back up sensing means for energizing said voltage controlled lens to the opaque state.

4. An eye protection device as defined in claim 1, wherein said voltage controlled lens means includes a plurality of separate lenses.

5. An eye protection device as defined in claim 1, wherein said voltage controlled lens means includes ordinary corrective lenses.

6. An eye protection device as defined in claim 4, wherein said detector means includes a plurality of detectors, each said detector independently controlling one of said lenses.

7. An eye protection device as defined in claim 1, wherein said voltage controlled lens includes multiple voltage controlled segment areas for independent energization of any said segment areas to an opaque state.

* * * * *